(12) United States Patent
De Jong et al.

(10) Patent No.: US 6,473,164 B1
(45) Date of Patent: Oct. 29, 2002

(54) SYSTEMS, APPARATUSES AND METHODS FOR DIAMOND COLOR MEASUREMENT AND ANALYSIS

(75) Inventors: Peter De Jong, Deurne; Ronald Geurts, Hove, both of (BE)

(73) Assignee: Gemological Institute of America, Inc., Carlsbad, CA (US)

( * ) Notice: Subject to any disclaimer, the term of this patent is extended or adjusted under 35 U.S.C. 154(b) by 0 days.

(21) Appl. No.: 09/505,981

(22) Filed: Feb. 16, 2000

(51) Int. Cl.$^7$ .............................................. G01N 21/00

(52) U.S. Cl. ......................... 356/30; 356/445; 356/446

(58) Field of Search ........................... 356/30, 31, 445, 356/446, 600

(56) References Cited

U.S. PATENT DOCUMENTS

| | | | |
|---|---|---|---|
| 3,744,919 A | 7/1973 | Babb | 356/189 |
| 3,794,424 A | 2/1974 | Eickhorst et al. | 356/30 |
| 3,858,979 A | 1/1975 | Elbe | 356/30 |
| 3,867,032 A | 2/1975 | Bruck | 356/30 |
| 3,944,368 A | 3/1976 | Beesley | 356/30 |
| 3,947,120 A | 3/1976 | Bar-Issac et al. | 356/30 |
| 4,033,683 A | 7/1977 | Tancredi | 353/7 |

(List continued on next page.)

FOREIGN PATENT DOCUMENTS

| | | |
|---|---|---|
| DE | 3600115 A1 | 7/1987 |
| EP | 0 041 348 A2 | 9/1981 |
| EP | 0 041 348 B1 | 9/1981 |
| EP | 0 147 002 B1 | 3/1985 |
| EP | 0 147 002 A2 | 3/1985 |
| EP | 0 611 160 A3 | 8/1994 |
| EP | 0 611 160 A2 | 8/1994 |

(List continued on next page.)

OTHER PUBLICATIONS

PCT Notification of Transmittal of International Preliminary Examination Report dated Mar. 29, 2002, and International Preliminary Examination Report for related Application PCT/US01/03869 (11 pages).

U.S. patent application application Ser. No. 09/687,659, Reinitz et al., filed Oct. 12, 2000.

U.S. patent application Ser. No. 09/687,759, Reinitz et al., filed Oct. 12, 2000.

Burridge, A.D., "Quarter Century of Diamond Research," Gems & Gemology (Fall 1972) 14(3): 66–77.

Collins, A.T., "Pitfalls in Color Grading Diamonds by Machine," Gems & Gemology (Spring 1984) 20(1):14–21.

(List continued on next page.)

Primary Examiner—Frank G. Font
Assistant Examiner—Roy M. Punnoose
(74) Attorney, Agent, or Firm—Gray Cary Ware & Freidenrich

(57) ABSTRACT

The present invention comprises systems, apparatuses and methods for measuring and analyzing gem color in a way which reliably and consistently simulates visual color analysis methodology. The preferred system embodiment of the present invention comprises several aspects, including the use of daylight approximating lamps, such as daylight-approximating fluorescent tubes or halogen lamp boosted with a filter to approximate daylight, and a light detector which directs light of a specific angle such that the system approximates visual analysis methodology. In the case of diamond analysis, in one embodiment, the system of the invention includes three major elements: a daylight-approximating light source that illuminates the pavilion side of the diamond, a light detector which detects light coming out at a specific angle from the pavilion side of the diamond, and an optical measurement device which measures the light detected by the light detector. In a preferred embodiment of the system, the daylight-approximating light source illuminates the pavilion side of the diamond through a diffuser. In another preferred embodiment, the light detector detects light which is coming from a rotating diamond.

37 Claims, 10 Drawing Sheets

U.S. PATENT DOCUMENTS

| | | | |
|---|---|---|---|
| 4,056,952 A | 11/1977 | Okuda | 63/32 |
| 4,152,069 A | 5/1979 | Bruck | 356/30 |
| 4,176,299 A * | 11/1979 | Thornton, Jr. | 315/326 |
| 4,186,838 A | 2/1980 | Levitt et al. | 209/581 |
| D257,617 S | 12/1980 | Wolkenfeld | 99/140 |
| 4,266,871 A | 5/1981 | Ritzi | 356/30 |
| 4,280,625 A | 7/1981 | Grobbelaar et al. | 209/582 |
| 4,291,975 A | 9/1981 | Raccah | 356/30 |
| 4,330,062 A | 5/1982 | Conway et al. | 209/582 |
| 4,461,568 A | 7/1984 | Welbourn et al. | 356/30 |
| 4,476,982 A | 10/1984 | Paddock et al. | 209/582 |
| 4,482,245 A | 11/1984 | Makabe et al. | 356/30 |
| 4,508,449 A | 4/1985 | Okazaki | 356/30 |
| 4,527,895 A | 7/1985 | Rubin | 356/30 |
| 4,534,644 A | 8/1985 | Beesley | 356/30 |
| 4,615,902 A | 10/1986 | Falcoff et al. | 427/8 |
| 4,647,194 A | 3/1987 | Shigetomi et al. | 356/30 |
| 4,875,771 A | 10/1989 | Bowley et al. | 356/30 |
| 4,907,875 A | 3/1990 | Bowley et al. | 356/30 |
| 4,951,825 A | 8/1990 | Hawkins et al. | 209/558 |
| 5,005,971 A | 4/1991 | Davis | 356/30 |
| 5,044,123 A | 9/1991 | Hoffman | 51/73 |
| 5,056,826 A | 10/1991 | Suwa | 283/67 |
| 5,064,281 A | 11/1991 | Davis | 356/30 |
| 5,118,181 A | 6/1992 | Yifrach et al. | 356/30 |
| 5,143,212 A | 9/1992 | Roberts et al. | 206/223 |
| 5,182,616 A | 1/1993 | Roberts et al. | 356/402 |
| 5,285,297 A | 2/1994 | Rose et al. | 358/518 |
| 5,335,293 A | 8/1994 | Vannelli et al. | 382/17 |
| 5,339,176 A | 8/1994 | Smilansky et al. | 358/504 |
| 5,422,711 A | 6/1995 | Can | 356/30 |
| 5,430,538 A | 7/1995 | Kobayashi | 356/30 |
| 5,515,157 A | 5/1996 | Can | 356/30 |
| 5,544,254 A | 8/1996 | Hartley et al. | 382/108 |
| 5,579,407 A | 11/1996 | Murez | 382/164 |
| 5,615,005 A | 3/1997 | Valente et al. | 356/30 |
| 5,801,819 A | 9/1998 | Spear et al. | 356/30 |
| 5,818,953 A | 10/1998 | Queisser et al. | 382/110 |
| 5,828,405 A | 10/1998 | Vanier et al. | 348/61 |
| 5,835,200 A | 11/1998 | Smith et al. | 356/30 |
| 5,835,205 A * | 11/1998 | Hunter et al. | 356/30 |
| 5,899,503 A | 5/1999 | Yoshizawa | 283/70 |
| 5,950,178 A | 9/1999 | Borgato | 705/37 |
| 5,966,673 A | 10/1999 | Shannon, Sr. | 702/35 |
| 5,983,238 A | 11/1999 | Becker et al. | 707/104 |
| 6,020,954 A * | 2/2000 | Aggarwal | 356/30 |
| 6,030,595 A | 2/2000 | Sumiya et al. | 423/446 |

FOREIGN PATENT DOCUMENTS

| | | |
|---|---|---|
| GB | 2 010 474 A | 10/1977 |
| GB | 2 036 360 A | 10/1978 |
| IL | 43465 | 12/1976 |
| JP | 57-204440 | 12/1982 |
| JP | 58-728 | 1/1983 |
| JP | 58-38843 | 3/1983 |
| JP | 58-92920 | 6/1983 |
| JP | 5-79993 | 3/1993 |
| JP | 7-333158 | 12/1995 |
| JP | 9-273994 | 10/1997 |
| JP | 11-255511 | 9/1999 |
| WO | WO 87/03963 | 7/1987 |
| WO | WO 88/05534 | 7/1988 |
| WO | WO 92/17388 | 10/1992 |
| WO | WO 96/07894 A1 | 3/1996 |
| WO | WO 96/23207 | 8/1996 |
| WO | WO 99/05629 | 2/1999 |
| WO | WO 99/61890 | 12/1999 |

OTHER PUBLICATIONS

Crowningshield, R., "Developments and Highlights at GIA's Lab in New York," Gems & Gemology (Fall 1973) 14(7):212–215.

Eickhorst, M., "Subjective and Objective Colour Grading of Diamonds," Diamond World Review (1977) 3:5/6.

Fritsch, et al., "The Identification of Zachery–Treated Turquoise", Gems & Gemology (Spring 1999) 35(1): 4–16.

Holmes, J., "Color Range Form Variations in Diamonds," Gems & Gemology (Summer 1947) 5(10): 430–446.

Huffer, H., "Okuda Diamond Color Grader," Jewelers' Circular–Keystone (Apr. 1983) pp. 48–50.

Hurlbut, C.S., Jr., "Causes of Color in Gemstones," Gems & Gemology (Summer 1949) 6(6). 170–179.

King, J., "Grading Fancy–Color Diamonds," Proc. of the International Gemological Symposium (1991) pp. 62–63.

King, J et al., "Characterizing Natural–Color Type IIB Blue Diamonds," Gems & Gemology (Winter 1998) 34(4):246–268.

King, J. et al., "Color Grading of Colored Diamonds in the GIA Gem Trade Laboratory," (Winter 1994) 30(4):220–242.

Lakowski, R., "Diamond Colour Grading: A Comparative Evaluation," Association Internationale Del La Couleur (1997), pp. 472–477.

Liddicoat, R. et al., "The Jeweler's Manual," Gemological Institute of America, pp. 28–41.

Liddicoat, R., "Developments and Highlights at GIA's Lab in Los Angeles," Gems & Gemology (Fall 1973) 14(7):200–207.

Loeffler, B. et al., "Shedding Light on the Color of Gems and Minerals," American Scientist (1976) 64:636–647.

Moses, T. et al., "A Contribution to Understanding the Effect of Blue Fluorescence on the Appearance of Diamonds," Gems & Gemology (Winter 1997) 33(4):244–259.

McCarthy, D., "Microspectometer Is a Diamond's Best Friend," Photonics (Mar. 2000) 34(3):66–67.

Nelson, J.B., "The Colour Bar in the Gemstone Industry," J. Gemm. (1986) 20(4):217–237.

Read, P., "Visual Colorimetry and Comparison Grading," J. Gemm. (1980) 17(1):29–42.

Read, P., Gemmological Instruments—2nd edition (1983) pp. 74–83.

Scarratt, K., "The Identification of Artificial Coloration in Diamond," Gems & Gemology (Summer 1982) 18(2):72–78.

Shigley, J. et al., "Measurement of Color in Faceted Gemstones," GIA World News, pp. 6–8.

Shipley, R. "Electronic Colorimetric for Diamonds", Gem & Gemology (Spring 1958) 9(5):136–143.

1998 Adamas Gemological Laboratory, SAS 2000 Spectrophotometer Analysis System, promotional material.

1998 Adamas Gemological Laboratory, SAS 2000 Spectrophotometer Analysis System, promotional material, original publication date unknown.

1996 Austron Digital Diamond Colorimeter, Operating Instructions.

1990 GIA GIL Gem Grading Report, promotional brochure.

1997 Gran Computer Industries, Inc., Model DC 2000fs Diamond Colorimeter, User Guide.

Jewelers Circular Keystone, Advertisement for Diamond Color Slide.

New York Diamonds, Autumn 1990, No. 10. Article: Inside the GIA, the quest for accuracy.

Hemphill T.S., Reinitz I.M., Johnson M.L., Shigley J.E. (Fall 1998) Modeling the appearance of the round brilliant cut diamond: An analysis of brilliance. *Gems & Gemology*, vol. 34, No. 3, pp. 158–183.

Manson D.V. (1991) Proportion considerations in round brilliant diamonds (abstract), A.S. Keller, Ed., *Facing the Future—Proceedings of the International Gemological Symposium*, Jun. 20–24, 1991, Los Angeles, p. 60.

Suzuki S. (1970) A new design for brilliance plus dispersion. *Australian Gemmologist*, vol. 10, No. 10, pp. 13–24.

Harding B.L. (1975) Faceting limits. *Gems & Gemology*, vol. 15, No. 3, pp. 78–87.

Dodson J.S (1978) A statistical assessment of brilliance and fire for polishing gem diamond on the basis of beometrical optics. Ph.D. Thesis, University of London.

Dodson J.S. (1979) The statistical brilliance, sparkliness and fire of the round brilliant–cut diamond. *Diamond Research*, 1979, pp. 13–17.

Tognoni C. (1990) An automatic procedure for computing the optimum cut proportions of gems. *La Gemmologia*, vol. 15, No. 3–4, pp. 23–32.

Kato M. (1982) Re–Examination of Optimum Cutting Angles Between Main Facets of Gemostones Based on Geometrical Optics. *Journal of the Gemmological Society of Japan*, vol. 9, No. 1, 3–17, pp. 127–142.

Kato M. (1991) Evaluation of brilliancy in relation to various combinations of the main facet angles. *Journal of the Gemmological Society of Japan*, vol. 16, No. 1–2, pp. 15–23 (and English translation).

Astric B., Merigoux H., Zecchini P. (1991) Etude theorique de l'aspect d'un diamant taille brilliant en fonction de ses parametres de taille. *Revue de Gemmologie a.f.g.*, No. 107, pp. 17–23 (and English translation).

Astric B., Merigoux H., Zecchini P. (1992) Etude de la vaariation de l'aspect de pierres taillees a l'aide d'image de synthese. *La Gemmologia*, vol. 17, No. 1, pp. 7–31 (and English translation).

Internet (http://www.rockhounds.com/rockshop/gem_designs/gemcad.html) GemCad, a computer program for modeling the appearance of faceted gemstones that has been available for several years (Product Review: GemCad 4.0: Rowland J., Originally Published in the Garnet Gazette Mar. 1994).

Internet (http://www.gemology.ru:8101/octonus) Octonus, a company at Moscow State University formed in 1991, that is involved with conducting research on the computer modeling of diamond appearance. This company sells a commercial computer program for light tracing in polished diamonds. They also present results of their research work on diamond appearance on this web site. Inventor first met representative of this group in Jun. 1999.

Internet (http://www.thunder.prohosting.com/~ultratec/ray.html) GEMRAY, Davis Designs, Strickland R. (last updated Aug. 8, 1999).

Walters G. (Dec. 1996) Cut Grading: Do the Numbers Add Up? Rapaport Diamond Report, vol. 19, No. 45, pp. 49–50.

Gilbertson A., Walters G. (Jan. 1997) What Tolkowsky Really Said. Rapaport Diamond Report, vol. 20, No. 2, pp. 35–37.

Gilbertson A., Walters G. (Feb. 1997) The Measure of Beauty, Rapaport Diamond Report, vol. 20, No. 6, pp. 43–46.

Gilbertson A. (Fall 1999) The Revolution in Cut Grading, Gems & Gemology, p. 157.

Gilbertson A., Walters G., Mcleod K., Wildman M. (1998), Letting Light Speak for Itself, Advancements in the Science of Cut Analysis, Diamond Profile Laboratory.

Lakowksi R. (Jul. 1977) C24 Diamond Colour Grading: A Comparative Evaluation, Color 77, Invited Lectures and Extended Abstracts of the Papers to be Presented at the Third Congress of the International Colour Association, Rensselaer Polytechnic Institute, Troy, New York, pp. 473–477.

Dodson J.S. (Apr. 1978) A Statistical Assessment of Brilliance and Fire for the Round Brilliant Cut Diamon, Optica Acta, vol. 25, No. 8, pp. 681–692.

Dodson J.S. (Apr. 1978) The Brilliance, Sparkliness And Fire Of Some Modifications To The Round Brilliant Cut Diamond Style, Optica Acta, vol. 25, No. 8, pp. 693–699.

Dodson J.S. (Apr. 1978) The Brilliance, Sparkliness And Fire Of Several Diamond Simulants, Optica Acta, vol. 25, No. 8, pp. 701–705.

Sten N. (1975) Computer Ray Tracing in Faceted Gemstones. Master of Science Thesis, Feinberg Graduate School of The Weizmann Institute of Science.

Kirkpatrick D. G., Walsh J. P. (Jun. 1985) The Geometry of Beam Tracing, ACM Proceedings of The Symposium on Computer Geometry, pp. 55–61.

Hanrahan R. (May 1986) Using Caching and Breadth–First Search to Speed Up Ray–Tracing (extended abstract), Proceeding of Graphic Interface' 86 and Vision Interface' 86, pp. 56–61.

Ghazanfarpour D. (Feb. 1992) Visualisation Realiste Par Lancer De Pyramides et Subdivision Adaptative, Proceedings of the $11^{th}$ International Conference of the CADCAM, Computer Graphics and Computer Aided Technologies, pp. 167–180 (and English translation).

Devillers O. (Sep. 1989) Tool to Study the Efficiency of Space Subdivision Structures for Ray Tracing, pp. 467–481.

Getto P. (1989) Fast Ray Tracing of Unevaluated Constructive Solid Geometry Models, Proceedings of GC International' 89, Springer–Verlag, pp. 563–578.

Glassner A. S. (Oct. 1984) Space Subdivision for Fast Ray Tracing, IEEE Journal of Computer Graphics and Applications, vol. 4, No. 10, pp. 15–22.

Heckbert P.S., Hanrahan P. (Jul. 1984) Beam Tracing Polygonal Objects, Computer Graphics—Proceedings of 1984 SIGGRAPH, vol. 18, No. 3, pp. 119–127.

Ohta M., Mackawa M. (1990) Ray–Bound Tracing for Perfect and Efficient Anti–Aliasing, The Visual Computer, International Journal of Computer Graphics, vol. 6, No. 3, pp. 125–133.

Picott K. P. (Mar. 1992) Extension of the Linear and Area Lighting Models, The IEEE Journal of Computer Graphics and Applications, vol. 12, No. 2, pp. 31–38.

Musgrave F. K. (Sep. 1987) A Realistic Model of Refraction for Computer Graphics, Master of Science in Computer and Information Sciences Thesis, UCSC–CRL–88–11.

Arvo J., Kirk D. (Jul. 1987) Fast Ray Tracing by Ray Classification, Computer Graphics—Proceedings of 1987 SIGGRAPH, vol. 21, No. 4, pp. 55–64.

Shoaff W., Recursive Ray Tracing, Jan. 12, 2000, http://www.cs.fit.edu/wds/classes/adv–graphics/raytrace/raytrace.html.

Yuan Y., Kunil T. L., Inamoto N., Sun L. (1988) GemstoneFire: Adaptive Dispersive Ray Tracing of Polyhedrons, The Visual Computer, International Journal of Computer Graphics, vol. 4, No. 5, pp. 259–270.

Cleary, J. G., Wyvill G. (1988) Analysis of An Algorithm for Fast Ray Tracing Using Uniform Space Subdivision, The Visual Computer, International Journal of Computer Graphics, vol. 4, No. 2, pp. 65–83.

Bauer M. (1968) Precious Stones, Dover Publications Inc.

Nelson J. B. (Jul. 1989) The Four Optical Attributes of a Diamond, The Journal of Gemmology, vol. 21, No. 7, pp. 434–447.

Wade F.B., Diamonds—A Study of the Factors that Govern Their Value, G. P. Putnam's Sons, The Knickerbocker Press, pp. 52–81.

Whitlock H. P. (Feb. 7, 1917) The Evolution of the Brilliant Cut Diamond, The Jewelers' Circular, vol. LXXIV, No. 1, pp. 115–121.

Dake H. C. (Jan. 1953) Proportions for the Brilliant Cut, The Gemmologist, vol. XXII, No. 258, pp. 17–18.

Inoue K., Quantification and Visualization of Diamond Brilliancy, Journ. Gemmol. Soc., Japan, vol. 20, pp. 153–167.

Lawrence J. (Mar./Apr. 1997) Slow Gear for New Technology, Diamond International, No. 46, pp. 57–63.

Kato M. (1987) Elucidation of the Scintillation, Journal of the Gemmological Society of Japan, vol. 12, No. 1–4, pp. 12–19.

Toriwaki J., Yokoi S. (1987) Rendering Gems by Computer Graphics, Journal of The Gemmological Society of Japan, vol. 12, No. 1–4, pp. 3–11.

Rogers D. F., Procedural Elements for Computer Graphics, $2^{nd}$ Edition, WCB McGraw–Hill 1998, Table of Contents and Chapters 4–5.

Woo M., Neider J., Davis T., OpenGL Programming Guide, 2nd Edition, Addison–Wesley Developers Press 1997, Tables of Contents and Chapters 2, 5, and 7.

Foley J. D., Dam A. V., Feiner S. K., Hughes J. F., Computer Graphics—Principles and Practices, $2^{nd}$ Edition, Addison–Wesley 1990, Table of Contents and Chapters 13, 15–16.

Hall R., Illumination and Color in Computer Generated Imagery, Springer–Verlag, New York 1989, Tables of Contents, Chapters 2–4, and Appendix I.

Long R., Steele N. (1984) *Facet Design*. Seattle Faceting Books, Mercer Island, WA.

* cited by examiner

SYSTEMS, APPARATUSES AND METHODS FOR DIAMOND COLOR MEASUREMENT AND ANALYSIS

FIELD OF THE INVENTION

The present invention relates to systems, apparatuses and methods for gem color measurement and analysis, and more particularly systems, apparatuses and methods for measuring and analyzing the color of a diamond in a manner that approximates visual measurement and analysis methodology.

BACKGROUND OF THE INVENTION

Diamonds and other gemstones are often analyzed based upon their visual appearance to the human eye. Indeed, a diamond's visual appearance to the human eye under natural or daylight-approximating light is a primary indicator of the quality of the diamond. Accordingly, because diamond quality is substantially based on human visual perception, diamond analysis requires the exercise of judgment, the formation of opinions and the ability to draw fine distinctions based on visual comparisons.

In practice, diamond quality analysis is optimally performed by a team of trained individuals who visually inspect a diamond for features such as inclusions and structural flaws. This time-intensive process involves numerous inspections, measurements and checks by each individual. The process also involves quality control and may include a variety of non-destructive tests to identify treatments, fillings or other defects that may affect the quality of a specimen. Finally, the process includes intensive visual comparison of the diamond with a reference set of diamond master stones that serve as a historical standard with respect to diamond color and clarity.

The foundation of diamond analysis comprises analysis of the Four C's (color, clarity, cut and carat weight), a method of analysis invented by the Gemological Institute of America (GIA). Two of the Four C's, color and clarity, are evaluated along a scale or continuum. In the case of colorless to light-yellow colored diamonds, an analysis is made along what is commonly referred to as the GIA D to Z scale. The GIA D to Z color scale, ranging from colorless to yellow, is an international standard which has been calibrated to GIA's master diamonds since its development.

As described above, the visual inspection process of diamond analysis is subtle, time consuming and requires trained and experienced individuals. As a result, many members of the jewelry and gem field have stated a need for an instrument that can approximately analyze a diamond's color according to the D to Z standard. Over the years, numerous mechanical instruments have been proposed to "measure" the color of a polished diamond. Yet, apart from the problems of calibration errors and electronic drift, these instruments have not reached the desired level of accuracy and repeatability due to various inadequacies. Moreover, these instruments have not approximated visual color analysis methodology in a manner that makes their results meaningful within the context of the historical analysis standards.

The history of mechanical gemstone color grading instruments dates at least back to the 1940's when Dr. Robert M. Shipley, founder of GIA, developed a simple calorimeter comprising a light source and an incrementally moveable, colored plastic wedge. The Shipley device positioned the colored wedge behind a static diamond mount, allowing the user to compare the color of the diamond against the colored wedge backdrop. The Shipley device thus acted as an aid to visual inspection, relying on the human eye instead of a mechanical light detector and the human brain instead of an optical measurement device and processor.

In the 1950's, Dr. Shipley invented the first non-visual gem color analysis instrument, a modified color comparator, comprising a tungsten filament lamp for a light source, a photo cell for a light detector, blue and yellow light filters, a static stone holder and an iris diaphragm that passes light through to the photo cell. According to the method of the Shipley Colorimeter, the instrument user placed the diamond table down over a diffuser plate so that the tungsten light was transmitted first through the diamond and then through the iris diaphragm to the photocell. The instrument user then made sequential measurements of transmitted light, first deploying the blue filter and then deploying the yellow filter. According to the method of the invention, the instrument user subsequently compared the two transmission magnitudes detected by the photocell and looked up the results in a table organized along the D to Z scale to determine the index of the diamond's color.

Although the Shipley Colorimeter provided a type of color standard for many years, that standard did not precisely correlate with historical visual analysis standards for several reasons. First, the geometric relationship between the diamond, the light source and the detector did not approximate that of visual diamond analysis. Second, the tungsten filament lamp, though of fair output stability, did not provide the type of daylight conditions which have been the standard for visual analysis of diamonds and other gemstones. Third, the photocell detector did not register each individual frequency in the spectrum of visible light, like the human eye, but rather tracked the change in an overall spectrum magnitude resulting from the change in light filters. Thus, although the Shipley Colorimeter provided a highly useful and innovative instrument for non-visual diamond color analysis, it did not precisely approximate visual analysis methodology. Moreover, during analysis, the diamond was static, not rotated, and the device did not average color over a 360° rotation.

In the 1970's, the Eickhorst Colorimeter and the Okuda Colorimeter introduced two new varieties of color measurement instruments. Although still based on the color comparator method of the Shipley Colorimeter, Eickhorst disclosed the concept of using a fiber optic couple to direct light to the light detector. Okuda disclosed the concept of a voltage-stabilized tungsten light source and an integrating sphere to direct light on the diamond. However, like the Shipley Colorimeter, these instruments relied on the tungsten filament lamps for their light source. Moreover, like the Shipley Colorimeter, the devices compared the overall magnitude of light transmitted by the diamond in response to the use of two different frequency filters. The Eickhorst and Okuda instruments furthermore directed the tungsten light into the crown facets of the diamond, rather than illuminating the diamond into its pavilion side, and did not subsequently measure the light coming out of the pavilion side, as is the case with visual diamond analysis.

In the 1980's, U.S. Pat. No. 4,508,449, to Okazaki, disclosed an apparatus for measuring the color of a brilliant cut diamond by using a spectrophotometer to measure a limited spectrum of light coming from a diamond. The instrument included an arithmetic unit for deriving tristimulus values X, Y and Z from the measured spectrum. Okazaki further disclosed the use of a xenon or halogen white light source and a type of filter (monochromater) to provide a beam of monochromatic light that is sequentially varied in frequency over a spectral band of interest. Okazaki further disclosed a method of recording the magnitude of light emanating from the diamond in response to sequentially changing frequencies within the spectral band of interest. Okazaki taught away from directing light into the pavilion side of the diamond in the manner of visual analysis (Col. 1, 11.38–39) and did not detect, either directly or indirectly, a specific angle of light coming from the diamond. Additionally, Okazaki's use of a photomultiplier tube and his sequential measurement of frequency response within the spectral band of interest creates an undesirable time delay in recording the transmission spectrum.

The 1990's have seen several variations in diamond color analysis instruments. For example, the Austron Colorimeter and the Gran Colorimeter disclosed the use of a photodiode as a light detector. Like their predecessors, the Austron and Gran Colorimeters used, respectively, halogen and tungsten lamps, and directed their illumination into the crown of the diamond. These instruments also did not rotate the diamond during measurement. Additionally, the instruments relied on the colorimeter comparison method of sequential filtering and, in the case of the Gran Colorimeter, compiled tristimulus color values.

Other instruments have incorporated spectrophotometers to improve consistency and accuracy in gemstone color analysis. For example, in 1992 Zeiss-Gubelin developed an instrument using a spectrophotometer. The Zeiss-Gubelin system transmitted light from a Xenon flash lamp via an integrating sphere into the pavilion facets of the diamond, placed table down, and indirectly detected a compilation of light coming from all angles from the pavilion facets of the diamond using the same integrating sphere. The Zeiss-Gubelin system also used a Xenon flash lamp to make a static measurement of diamond color.

Later spectrophotometric systems, including the Rennilson-Hale Gemstone Colorimeter, the Lamdaspec Spectrophotometer, and the Gran Spectrophotometer (DC2000FS) made use of Tungsten, Halogen and/or Xenon lamps. Although these systems were capable of detecting and analyzing the full spectrum of light, the instruments themselves failed to respect the geometric relationships used for visual diamond analysis. Moreover, none of the systems deployed a dynamic color analysis technique involving a rotation of the diamond. The systems furthermore did not average color over a rotation of the diamond.

An Adamas system, which performs color analysis and deploys a spectrophotometer, has been developed. However, the Adamas system illuminates through the table of the diamond, uses an integrating sphere and analyzes color using a single, static measurement. The instrument further does not approximate visual color analysis methodology, and does not meaningfully correlate the results to historical precedents of visual diamond analysis.

What is needed is a simple system and instrument which reliably and consistently approximates historical visual analysis methodology, including, for example, detection methodology, light source composition, illumination angles, and the use of historical visual analysis standards in order to correlate instrument results with historical precedents. There is further a need for a system and instrument with a stabilized output of daylight-approximating light, which can compensate for electronic drift, and which can reduce the hindering effects of light dispersion and direct reflection which occur when mechanically simulating visual detection methodology. Existing devices are inadequate for these purposes.

SUMMARY OF THE INVENTION

The present invention comprises systems, instruments and methods for analyzing gem color in a way which reliably and consistently simulates visual color analysis methodology. The preferred embodiment of the present invention comprises several aspects, including the use of daylight-approximating lamps, such as daylight-approximating fluorescent tubes, and a geometry which simulates the results of visual analysis. In the case of non-fancy-colored diamond analysis, in one embodiment, the system includes three major elements: a daylight-approximating light source that illuminates the pavilion side of the diamond, a light detector which detects light coming out of the pavilion side of the diamond at a specific angle, and an optical measurement device which measures the light detected by the light detector. In another embodiment, a measurement chamber encloses the diamond to be analyzed and the daylight-approximating light source illuminates the pavilion side of the diamond through a diffuser. Although a variety of light detectors and optical measurement devices may be used in the present invention, in a preferred embodiment the light detector comprises a fiber optic cable connected to a diode-array, and the optical measurement device comprises a spectrophotometer. In another preferred embodiment of the invention, the system further comprises a fourth element: an optical analysis mechanism, such as a data processor, that compares measurement data from the optical measurement device to a historical precedent and/or converts the measurement data into CIE color space.

According to one embodiment of the invention, the system includes four elements: a daylight-approximating light source that illuminates the pavilion side of a diamond, a rotor which rotates the diamond during illumination, a light detector and an optical measurement device which measures the light detected by the light detector. In a preferred variation of this embodiment, the optical measurement device measures light which the detector has detected coming from the diamond at a specific angle relative to the table of the diamond during the course of a single rotation of the diamond.

The various elements of the invention disclosed herein may be provided as separate pieces or as a single unit. For example, in the previously described embodiment, the light source may form part of an integrated unit with the rotor or alternately be provided separately. In another embodiment, the light detector and the optical measurement device may comprise an integrated unit with the light source and the rotor. The integrated unit may further comprise an optical analysis mechanism. Likewise, elements of the light detector may be part of the same unit as the optical measurement device, as in the case of a diode-array spectrophotometer, or may be provided separately.

In order to overcome difficulties associated with visual analysis geometry, a preferred embodiment of the invention includes at least one of several innovations to increase system stability and reliability. In a preferred embodiment, the system includes high frequency ballast in order to stabilize the daylight-approximating light source. Likewise, in another preferred embodiment, the system includes a light diffuser between the light source and the gemstone which serves to reduce the hindering effects of dispersion and direct reflections caused by the kind of illumination used in visual color analysis. In another preferred embodiment, the invention includes a mechanism to process a plurality of separate light spectrum measurements taken over the course of rotation of a gemstone. According to this preferred embodiment, the invention comprises a rotor platform that optionally has a stabilization ring to ensure its consistent rotation. In another embodiment, designed to overcome difficulties associated with electronic drift, the invention includes a correct-for-drift feature which may operate either statically or dynamically.

The methods of the present invention generally relate to the use of a system and instrument to analyze the color of a gemstone according to historical precedent. In accordance with one aspect of the method, the method of the invention comprises the steps of illuminating a gemstone with daylight-approximating light, detecting the light coming from a specific angle from the gemstone, measuring the detected light with an optical measurement device, analyzing the measurement data with an optical analysis mechanism, and indicating the color of the gemstone according to historical precedent.

According to another aspect of the method of the invention specifically applicable to diamond analysis, the method comprises the steps of illuminating the pavilion side of a diamond with daylight-approximating light, detecting the light that is coming out of the pavilion side of a table-down diamond at a specific angle relative to the table of the diamond, measuring the detected light with an optical measurement device and comparing the measurement data against historical precedent. According to another aspect of the method of the invention, the method comprises the steps of placing a diamond on a rotor platform, illuminating the pavilion side of the diamond with daylight-approximating light, rotating the rotor platform, detecting the light that is coming out of the pavilion side of the diamond at a specific angle relative to the table of the diamond during rotation, measuring the detected light with an optical measurement device and analyzing the measurement data.

As for systems and instruments, it is one object of the invention to increase the ease by which individuals may obtain substantially reliable gemstone color analysis. It is another object of the present invention to overcome the difficulties associated with the application of visual analysis geometry to a mechanical analysis system. It is another object of the invention to provide a stable and reliable system for gem color analysis. It is another object of the invention to reduce dispersion and direct reflection during gem color analysis.

As for the methods of the invention, it is an object of the invention to provide a method of color analysis performable by individuals with little technical training or experience in gemology. It is a further object of the invention to provide methods which permit such individuals with little technical training or experience in gemology to reliably and consistently obtain semi-automated color analyses according to visual color analysis methodology.

BRIEF DESCRIPTION OF THE DRAWINGS

Reference is next made to a brief description of the drawings, which are intended to illustrate gemstone color analysis systems and instruments for use as disclosed herein. The drawings and detailed description which follow are intended to be merely illustrative and are not intended to limit the scope of the invention as set forth in the appended claims.

DETAILED DESCRIPTION

Figure 1:
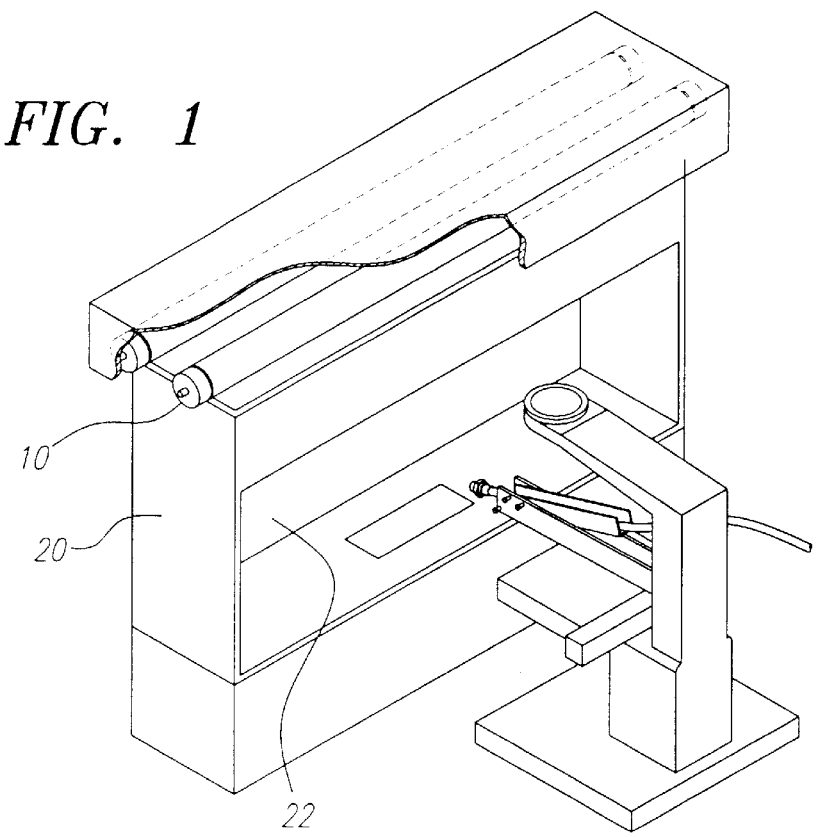
FIG. 1 depicts a light box which is illuminated overhead by daylight-approximating fluorescent lamps (high frequency ballast not shown).

FIG. 1 shows one embodiment of part of the system of the present invention as disclosed for use herein. In this embodiment, the system comprises at least one daylight-approximating lamp 10 which provides a light source akin to that used for visual color analysis of diamonds. According to this embodiment, the light source is positioned in a light box 20 and provides overhead illumination for a gemstone (not shown) contained within the light box. The light box of FIG. 1 may be of any size capable of containing a light source and a diamond or other gemstone. In the embodiment shown in FIG. 1, the daylight-approximating lamp is a daylight-approximating fluorescent lamp used in visual color analysis such as an Osram Biolux 72, Verilux F20T12 or Gretag Macbeth F20T1265. However, other lamps with a color temperature of between 5500 and 6500 Kelvin having a high color rendering index, preferably of at least 95, may be beneficially employed. The light box has the approximate length of the preferred daylight-approximating fluorescent lamp. The interior 22 of the light box 20 preferably has either white or light gray walls.

According to another aspect of the invention, the system novelly creates illumination by modifying a halogen light source having a high color temperature, preferably above 4000 Kelvin, and a filter that boosts the color temperature to daylight equivalence, preferably between 5,500 to 6,500 Kelvin. According to this aspect of invention, the illumination source may comprise a halogen lamp, preferably with a stabilized power supply, and boosted by a daylight correction filter such as a Schott filter BG26/2 mm to approximate daylight conditions.

Figure 2:
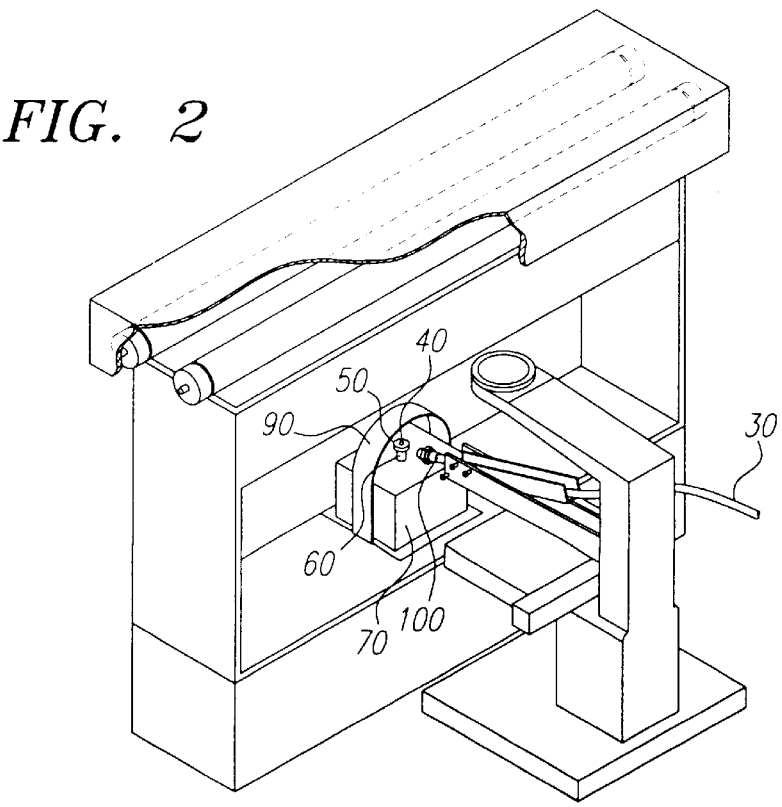
FIG. 2 shows an angle perspective view of a light sensing fiber optic cable of a simplified embodiment of the present invention with the cable directed at an angle of between zero and approximately forty-five degrees relative to the table of the table-down diamond when the diamond is accommodated on the rotating platform. The rotating platform and diffuser are shown within the light box of FIG. 1.

FIG. 2 shows a simple embodiment of the measurement instrument of the present invention along with the light source and light box of FIG. 1. According to this simplified embodiment of the measurement instrument, a light detector comprising fiber optic cable 30 is directed, at an angle of between zero and approximately forty-five degrees, at the pavilion facets of a diamond 40 which is positioned table-down on a rotor platform 50. The rotor platform 50 is in turn connected by a stabilizer column 60 to rotor 70. The rotor platform 50 is shown in FIG. 2 within the light box 20 with the light from lamp 10 transmitted by diffuser 90 in the direction of pavilion facets of the diamond 40. This form of diffused transmission serves to reduce the hindering effects of direct light reflections and dispersion and substantially facilitates detection of specific angles of light coming from the diamond which approximates visual analysis methodology.

According to one embodiment, the diffuser 90 is made of thin polytetrafluorethylene (PTFE), although other suitable equivalent diffusing materials may be used. In a preferred embodiment, the diffuser is made of Teflon® of a thickness of between 0.06 and 1.0 mm, and in the most preferred embodiment is made of Teflon® of a thickness of 0.4 mm. Rotor 70 preferably comprises a continuous duty motor, such as a synchronic 3 Watt AC continuous duty motor. In a most preferred embodiment, rotor 70 rotates at a speed of 20 rpm although a number of rotation speeds can be used provided they are coordinated with the measurement and analysis components of the system. As shown in FIG. 2, the light detector comprising fiber optic cable 30 further comprises collimator 100. However, although the light detector preferably comprises a fiber optic cable 30 with collimator 100, other light detectors suitable to approximating visual analysis methodology may be used. As shown in FIG. 2, for reasons of stability, rotor platform 50 is preferably circular in cross-section. However, other platform shapes may be used. Likewise, although FIG. 2 shows rotor 70 and the light detector comprising fiber optic cable 30 as physically unconnected, they may form part of an integrated measurement instrument. (See FIG. 5).

Figure 3:
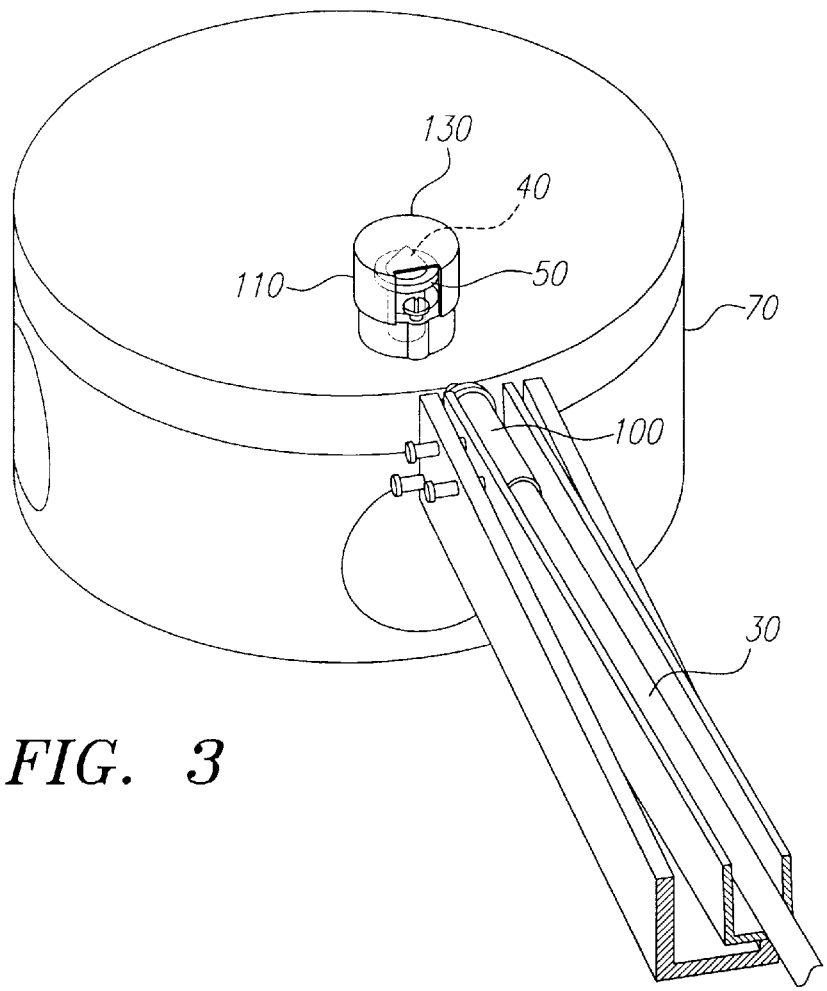
FIG. 3 shows an angle perspective view of a simplified embodiment of the present invention wherein the diamond is positioned, table-down, on a rotor platform, wherein the rotor platform is enclosed by a measuring chamber. A diffuser separates the light source (not shown) and the diamond.

FIG. 3 shows an angle perspective view of an embodiment of the measurement instrument of the present invention wherein the diamond 40 is accommodated, in a table-down position, by a surface, rotor platform 50. In FIG. 3, rotor platform 50 is rotatably connected to rotor 70. Rotor platform 50 is also enclosed by measuring chamber 110 and diffuser 130, said diffuser preferably located near to the diamond 40 between the light source (not shown) and the diamond. As in the embodiment shown in FIG. 2, the diffuser 130 is preferably made of a thin white Teflon® material which diffuses the light transmitted from above the diamond. According to a preferred embodiment, the measurement chamber 110 and rotor platform 50 are made of a reflective material, more preferably a diffuse, reflective material, and most preferably a diffuse, white reflective material such as polytetrafluorethylene (PTFE). Other materials such as barium sulphate or Spectralon® may be used provided they have minimal specific absorption in the visible and near UV spectrum. In a preferred embodiment, the material also does not fluoresce to ultra-violet radiation. In the embodiment shown in FIG. 3, the diffuser 130 is connected to the top of the measurement chamber 110 so that it at least partially seals the top of the measurement chamber. As shown in FIG. 3, the measurement chamber is preferably a cylinder with a circular cross-section. Alternatively, the measurement chamber may have another cross-sectional shape. According to the embodiment of FIG. 3, the light source (not shown) illuminates diamond 40 from its pavilion side, while rotor platform 50 rotates and the light detector, comprising fiber optic cable 30, detects the light coming out at a specific angle from the pavilion side of the rotating diamond.

Figure 4:
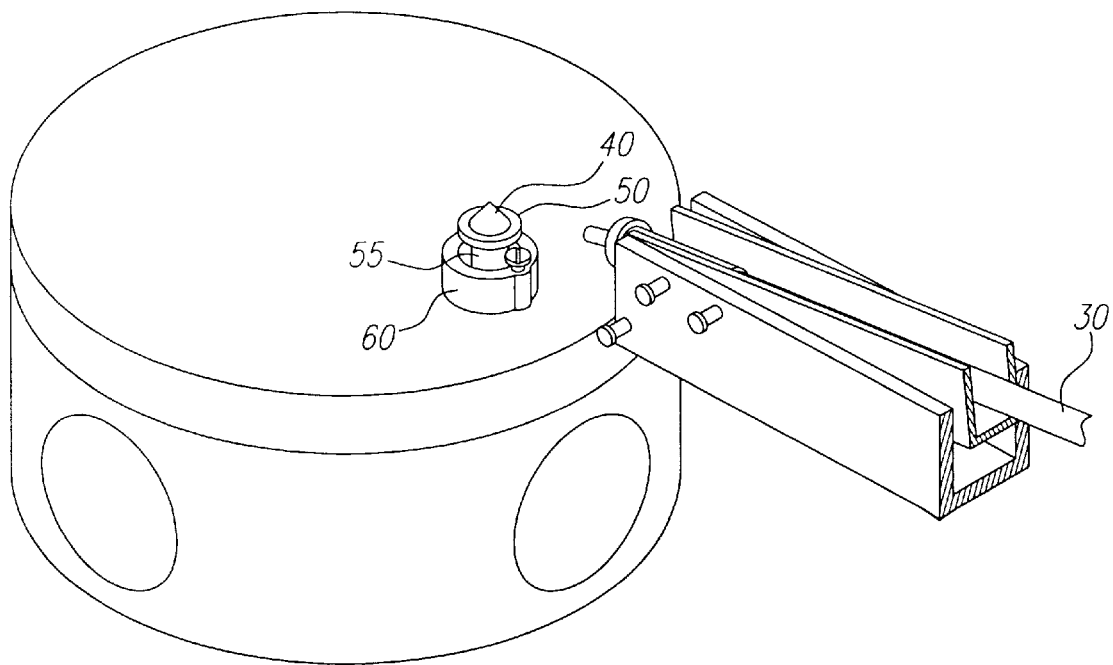
FIG. 4 shows the embodiment of FIG. 3 without the measuring chamber and diffuser.

FIG. 4 shows the embodiment of FIG. 3 with the measurement chamber 110 and diffuser 130 removed. The geometric relationship between diamond 40, rotor platform 50 and the light detector comprising fiber optic cable 30, approximates the geometry of visual color analysis methodology. The rotor platform 50 may optionally be stabilized by a circular stabilizing column 60 wherein the column stabilizes the base of a rotating rod 55 connected to rotor platform 50. Rotor platform 50 preferably has a slightly hollow top portion so that it can more securely accommodate a table-down diamond. Most preferably, rotor platform 50 has a slope of approximately three degrees from its center to each point on its circumference in order to stabilize the diamond during rotation. The stabilizing column 60 may be of various heights and may even extend past the horizontal plane of the rotor platform 50. The stabilizer column may also support the measurement chamber 110 when the measurement chamber is deployed. Although the surface accommodating the diamond is shown as a platform, other types of surfaces, such as the instrument base itself, may be used to accommodate the diamond.

In a preferred embodiment, the platform doubles as a white reference for calibration purposes. According to this embodiment, the user takes calibration readings based on detection of light coming from the platform with the gem removed. The user then may recalibrate the measurement device, such as by pressing a button on a spectrophotometer, should the reading change between gem analyses. Alternatively, the calibration readings and/or recalibration of the instrument may occur automatically between gem analyses.

Figure 5:
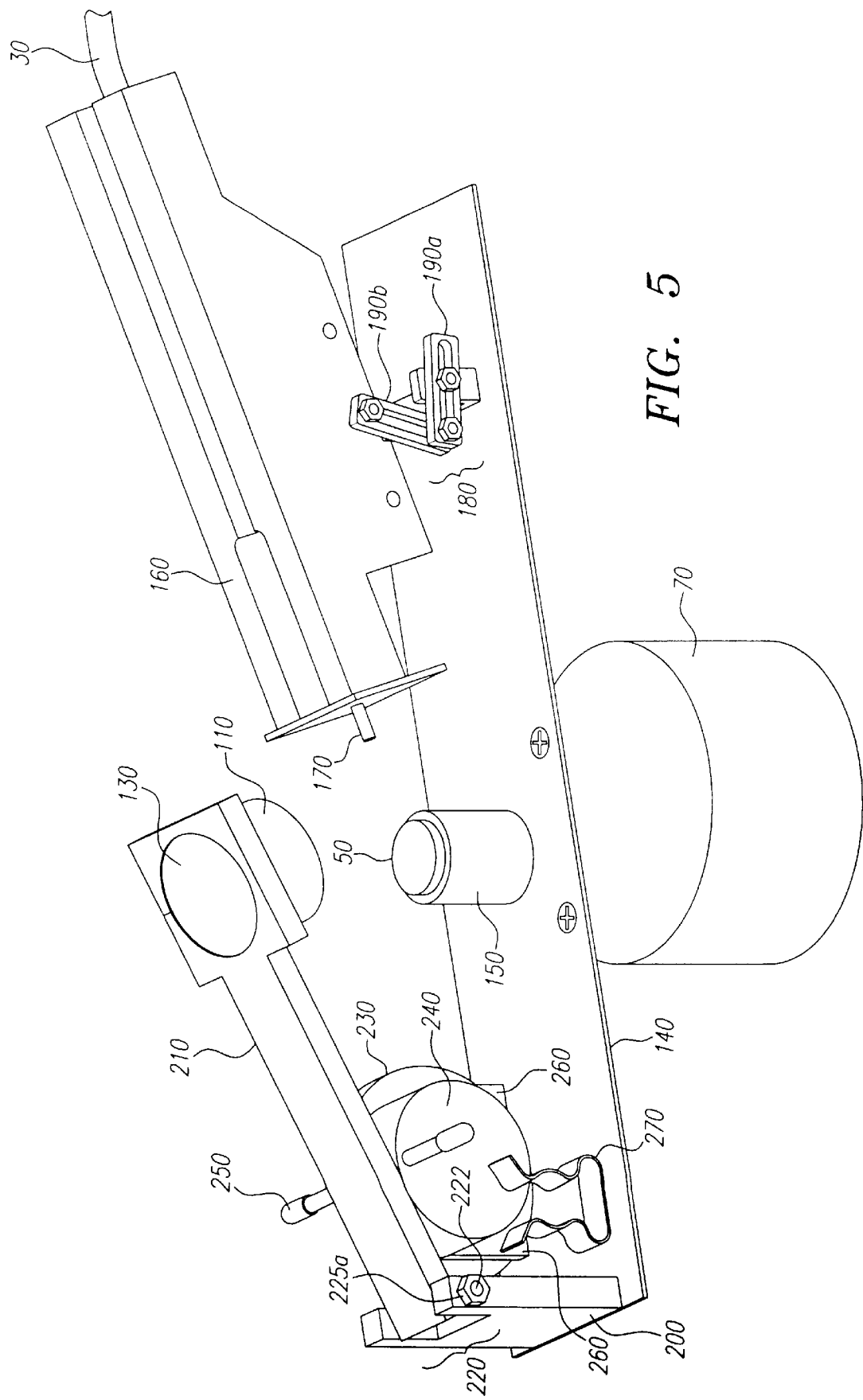
FIG. 5 shows an angle perspective view of a preferred integrated unit embodiment of the invention wherein a fiber optic cable is contained in a light sensor housing and positioned at an angle between zero and approximately forty-five degrees above the rotor platform.
Figure 9:
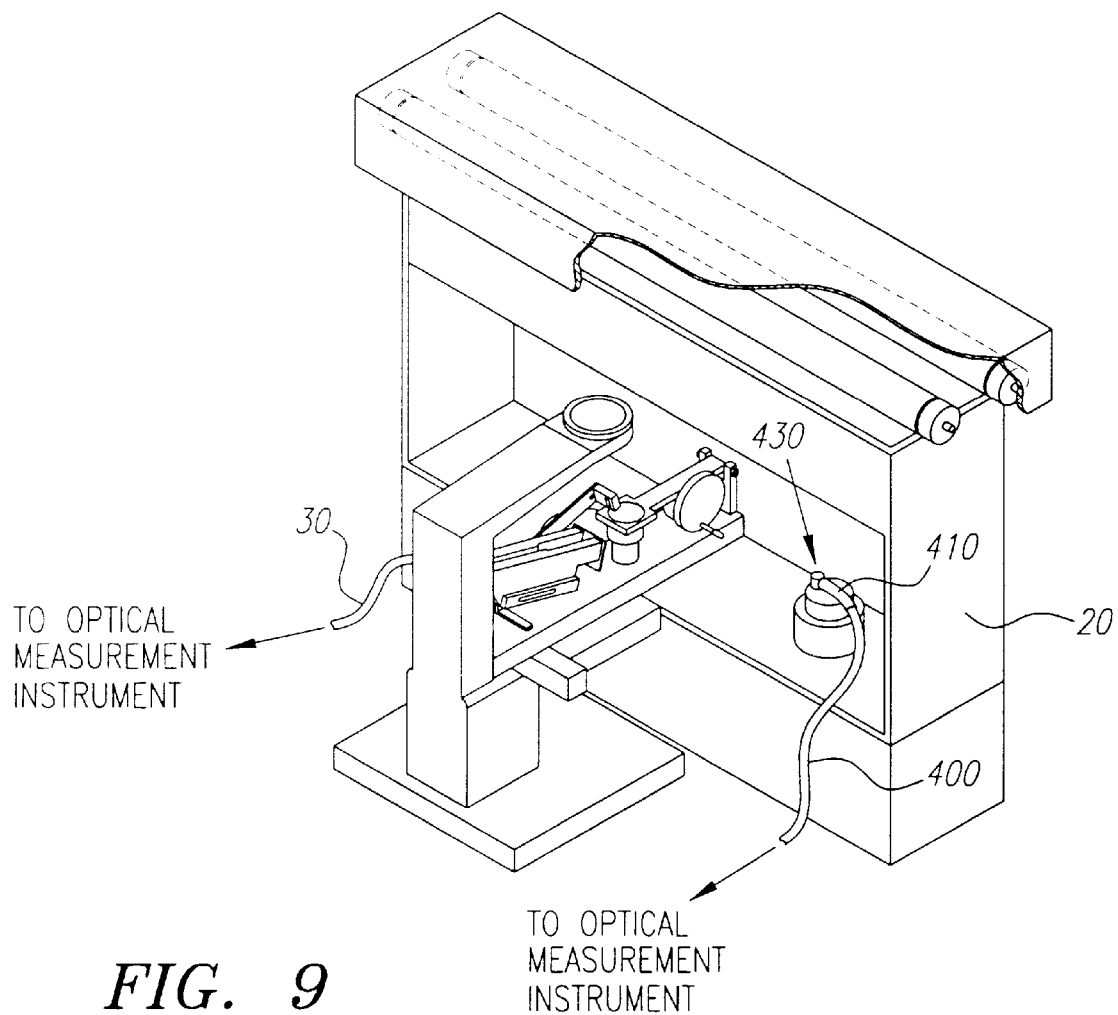
FIG. 9 shows a composite view of an embodiment of the present invention with a correct-for-drift feature comprising a second fiber optic cable directed at an angle between zero and approximately forty-five degrees into a reference material measurement chamber and reference platform made of the same material and having the same diffuser as the measurement chamber and rotor platform.

In a preferred embodiment of the measurement instrument portion of the invention, shown in FIG. 5, fiber optic cable 30, rotor 70, the rotor platform 50 and the measurement chamber 110 are all integrated on a base 140. Thus, the rotor, rotor platform and light detector are part of an integrated unit that maintains the proper geometrical relationships conforming to visual color analysis methodology. As shown in FIG. 5, the rotor platform 50 may form a unit with cylinder 150 which stabilizes the rotation of the rotor platform. The fiber optic cable 30 (not shown) is preferably contained in light detector housing 160 such that the detecting end of the diamond cable is positioned at an angle between zero and approximately forty-five degrees above where a table would rest on the rotor platform 50. The light detector housing 160 may have a collimator (not shown) and a light conduit 170 to ensure the correct angle of light coming from the gem is detected. An optional angle adjust mechanism 180 may be altered to change the angle of light detection by the light detector. In the embodiment shown in FIG. 5, the angle adjust mechanism 180 comprises a plurality of slotted armatures 190a and 190b. The angle adjust mechanism may optionally be connected to an angle direction read-out (not shown) which may be either analog (as shown in FIG. 9) or digital. In an alternate embodiment, the light detector may rotate around a stationary diamond-accommodating surface to detect light coming from the diamond.

According to a preferred embodiment of the invention, the light detector detects light directly coming from the diamond at a specific angle relative to the table of the diamond. In the case of non-fancy-colored diamonds, the specific angle of light detected is preferably between zero and approximately forty-five degrees relative to the table of a table-down diamond. Although other angles of detection may be used, such angles are not preferred to the extent they do not approximate visual analysis methodology. However, according to a preferred embodiment, the detector may detect light coming out of the pavilion side of a non-fancy-colored diamond at more than one angle, either sequentially or simultaneously, but within a specific angle range, preferably within zero to approximately forty-five degrees relative to the table of a table-down diamond. According to this embodiment, the detection of a plurality of angles within a specific angle range may be accomplished by a variety of techniques, including moving the detector during detection, using additional detectors, using a wide angle detector, and/or tilting the platform or other gem-accommodation surface during detection. If the detection of a plurality of angles within a specific angle range occurs sequentially for a rotating gemstone, then the sequential change in angle preferably occurs after a complete rotation. In the case of simultaneous detection, for a rotating non-fancy-colored diamond the detector or detectors preferably detect a plurality of angles within the specific angle range during the course of a single rotation.

According to the preferred embodiment, the light detector detects light coming from a specific angle from the diamond at an identifiable distance relative to the center of a table-down diamond. For non-fancy-colored diamonds that distance is preferably between 10 mm to 50 mm from the center of a table-down diamond. If a collimator or other detection-narrowing device is used, the preferred distance from the diamond will increase as the field of detection narrows. Likewise, within the preferred ranges, the distance may also increase with the narrowing of the fiber diameter. Similar adjustments within the preferred ranges may be made, for example, to adjust for the particular height selected for the rotor platform or adjust for diamond size and position. Minor adjustments may optionally be made to adjust to changes in the diameters of the measurement chamber and the platform or changes in the distance of the diffuser from the gemstone. Although the specific angle of light from the gem to be detected may be detected indirectly, such as by the use of a reflecting mirror, direct detection such as shown in FIG. 5, is preferred.

Figure 6:
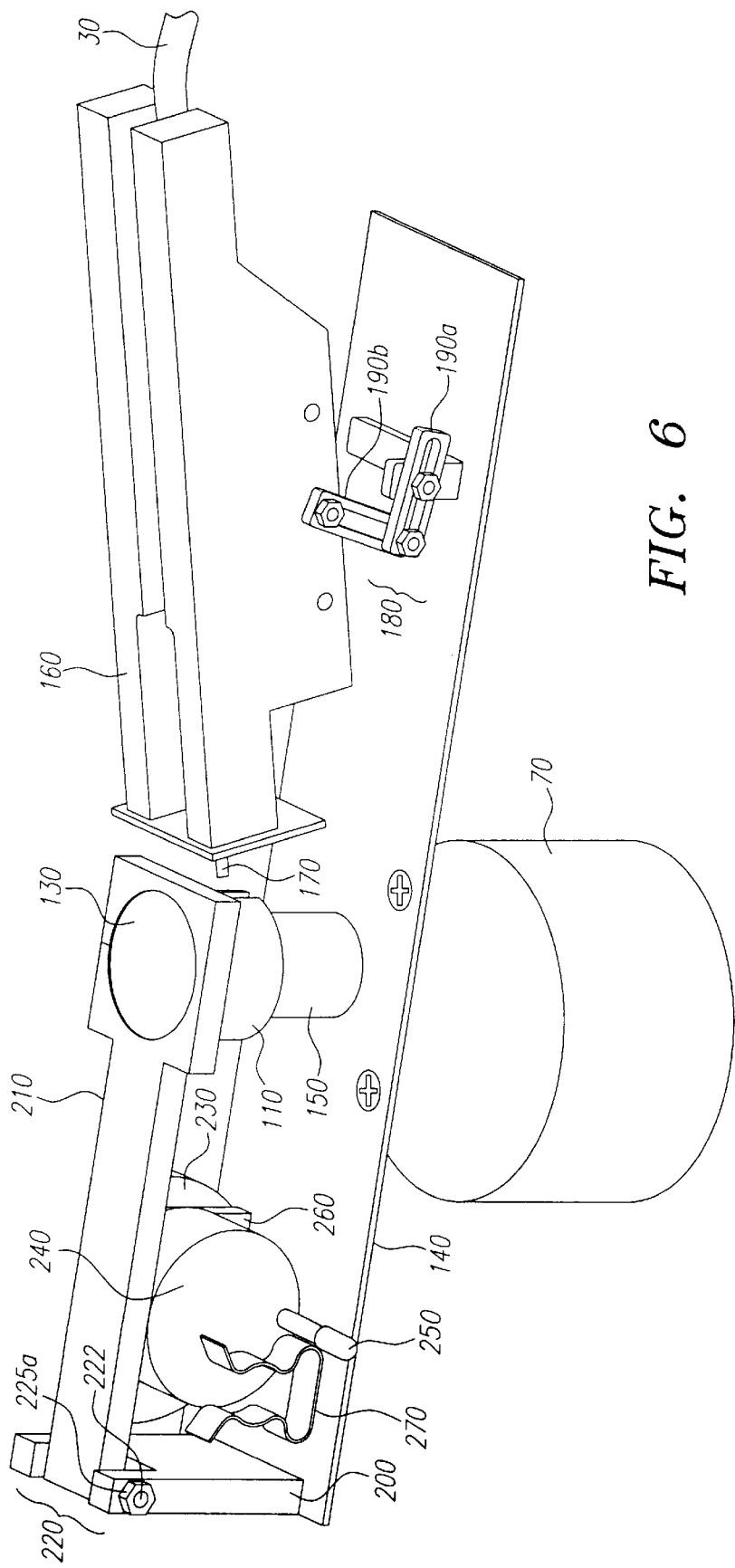
FIG. 6 shows the embodiment of FIG. 5 with the measuring chamber in the fully deployed position.

In FIG. 5, the preferred measurement instrument comprises a moveable measurement chamber 110 having an armature 210 and a diffuser 130. The moveable measurement chamber 110 may be withdrawn in order to permit access to the rotor platform 50 during gem placement and gem removal. Conversely, as shown in FIG. 6, the moveable measuring chamber 110 may be deployed to cover rotor platform 50 during light detection and stabilize its rotation. As shown in FIG. 5, the armature 210 is connected to stationary mount 200 by movement joint 220 wherein movement joint 220 comprises a metal bar 222 running horizontally through armature 210 and stationary mount 200. The metal bar 222 is secured on the sides of the stationary mount 200 by nuts 225a and 225b respectively (not shown). The coupling of the armature 210 and the stationary mount 200 permit controlled movement of the armature 210 and moveable measurement chamber 110 between deployed and non-deployed positions.

According to one aspect of the invention, the measurement instrument provides for steady, consistent movement of the armature and the moveable measurement chamber, and ensures a precise range of motion for the measurement chamber so as to maintain the proper geometric relationships during measurement. This aspect of the invention also prevents unwanted contact between the rotor platform and the moveable measurement chamber during light detection. To these ends, an embodiment of the measurement instrument of the present invention, shown in FIG. 5, has a rotating wheel couple comprising a centered large wheel 230 coupled to a non-centered small wheel 240 and a positioning bar 250 running horizontally through both wheels, parallel to base 140. According to the embodiment shown in FIG. 5, the two wheels are not concentric such that rotating both wheels by moving positioning bar 250 in a circular motion results in the small wheel 240 gradually increasing or decreasing its distance from the base 140, depending on whether the motion of the positioning bar 250 is clockwise or counterclockwise. In the embodiment shown in FIG. 5, the armature 210 rests across the width of the small wheel 240. By moving the wheels 230 and 240 using the clockwise circular motion of the positioning bar 250, the armature 210 and measuring chamber 110 will gradually and steadily be lowered into the deployed position as shown in FIG. 6. Conversely, the armature 210 may be raised into the non-deployed position by a counter-circular motion of positioning bar 250 as shown in FIG. 5.

According to the embodiment of FIG. 5, the positioning bar's movement is restrained by a slotted track (not shown) located in a coupling piece 260 which couples the two wheels 230 and 240. The positioning bar 250 is rotated through the track (not shown) until the positioning bar reaches stop 270, at which point the moveable measuring chamber 110 is fully deployed above the rotating platform 50. Stop 270 thus prevents the moveable measurement chamber 110 from being lowered in a manner which would interfere with the path of detection for the light detector, the rotation of the rotor platform or the proper geometric measurement relationship between the various elements of the measurement instrument. In a preferred embodiment, the moveable measurement chamber may be locked into position during light detection. The embodiment of FIGS. 5 and 6 thus beneficially uses the motion of coupled wheels 230 and 240, and the stop 270 to achieve steady and consistent placement of the moveable measurement chamber. However, other mechanical mechanisms as are known in the art may be used to achieve the same result.

Figure 7:
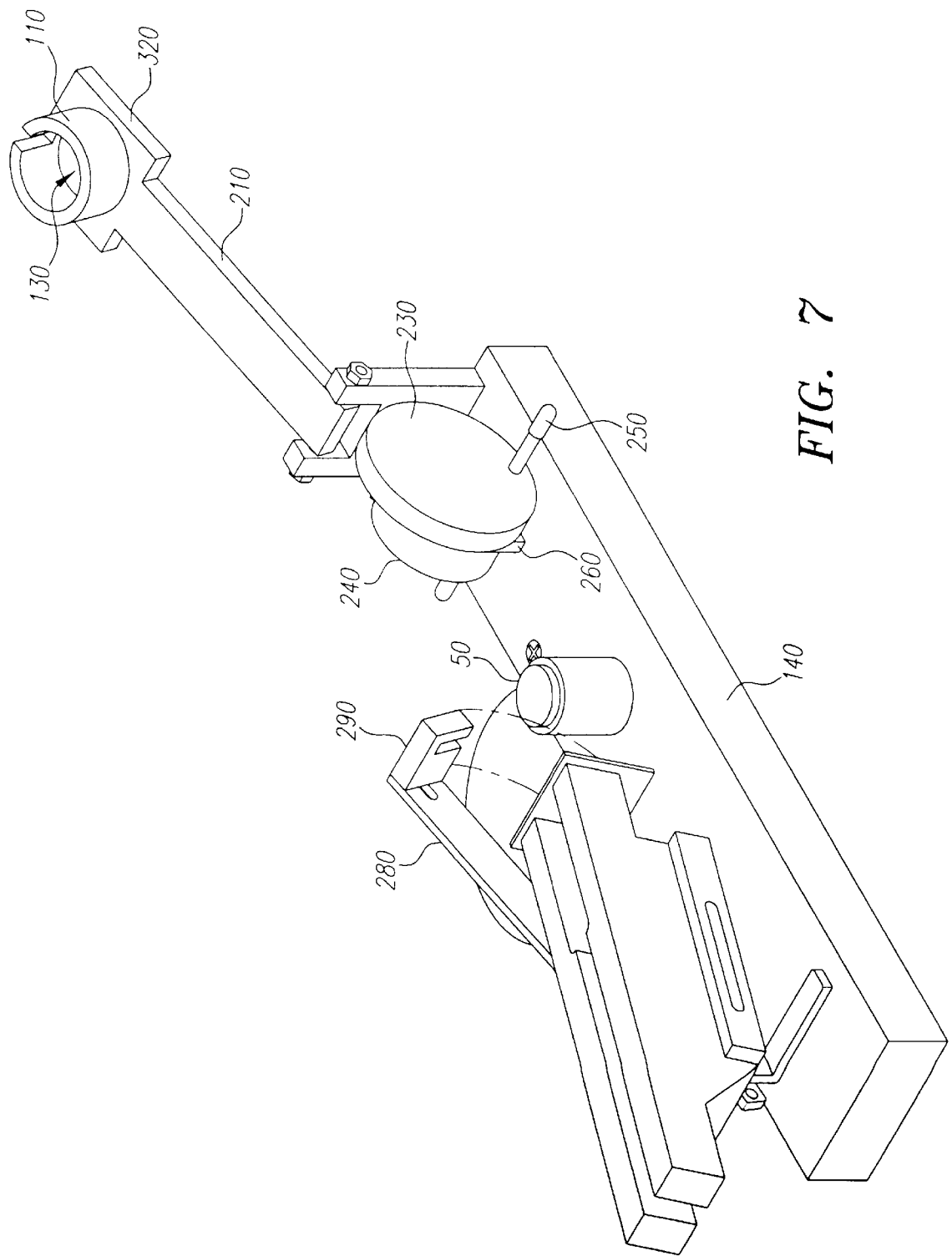
FIG. 7 shows an angle perspective view of an alternate embodiment of the invention wherein the invention comprises a swingle arm having a dark reference that enables a dark reading as part of a calibration procedure.
Figure 8:
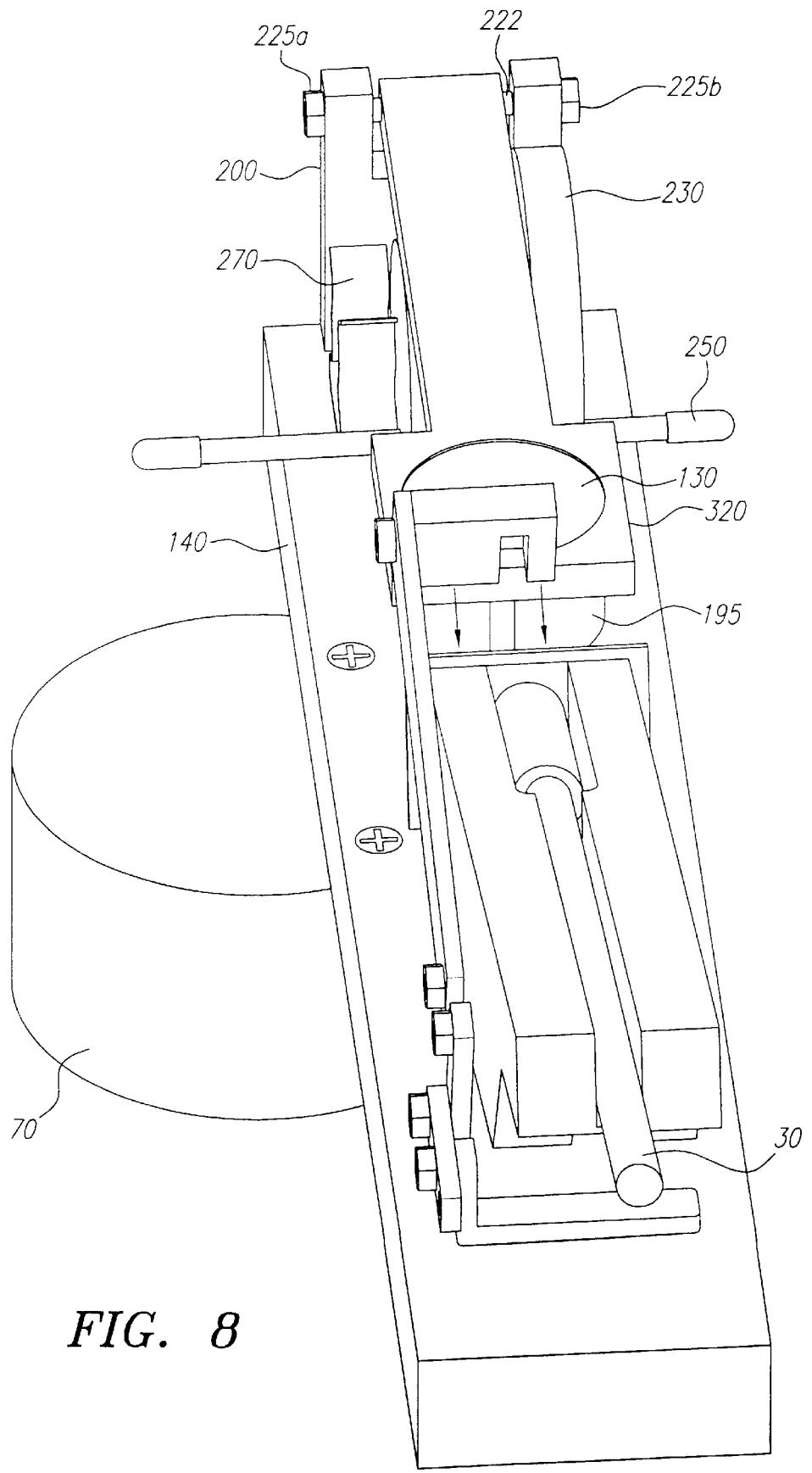
FIG. 8 shows a top angle perspective view of the alternate embodiment of FIG. 7 where the swingle arm is in the nearly closed position.

FIG. 7 shows an angle perspective of an alternate embodiment of the invention wherein the invention comprises a swingle arm 280 having a dark reference 290 for purposes of measurement calibration. The swingle arm 280 may be movably attached to the base 140 such that it may be moved from the non-deployed position shown in FIG. 7 to the deployed position, shown nearly deployed in FIG. 8. FIG. 8 demonstrates the embodiment of FIG. 7 with the deployed swingle arm 280 beginning to place the dark reference 290 over the light detector conduit 170 (not shown) so that the user can take a dark reading.

In the embodiment shown in FIG. 7, the measurement chamber 110 is shown in the non-deployed mode. The measurement chamber 110 is a hollow cylinder, with an opening in its side which enables light from the chamber to reach the light detector. As shown in this embodiment, the measurement chamber 110 is also integrated with the armature 210. However, the measurement chamber and armature may alternately be provided as separate pieces. As further shown in the embodiment of FIG. 7, the measurement chamber 110 is covered by diffuser 130 which is integrated within armature head 320. Alternately, the diffuser 130 may simply cover the measurement chamber without the need for an armature head. Moreover, although FIG. 7 discloses a moveable measurement chamber, in an alternate embodiment, the measurement chamber is stationary and the light detector is moveable to permit placement and removal of the gemstone.

In another embodiment of the present invention, shown in FIG. 9, the system includes a correct-for-drift feature comprising a second light detector further comprising a fiber optic cable 400, directed at an angle between zero and approximately forty-five degrees at reference material measurement chamber 430 and a reference platform (not shown). The reference chamber 430 and reference platform (not shown) are made of the same material and preferably use the same type of diffuser as the primary measuring chamber and rotor platform. The second light detector comprising fiber optic cable 400 is positioned at the same angle with respect to the reference platform as the first light detector comprising fiber optic cable 30 is positioned relative to rotor platform 50. The correct-for-drift feature may either statically or dynamically provide data to either a data processor and/or optical measurement device which in turn corrects the system for electronic drift and/or interference. The correct-drift-feature may be included as an integrated part of the measurement instrument or may be provided separately as shown in FIG. 9. Preferably, the correct-for-drift feature makes use of the same light source and angle of illumination as the primary measurement chamber. Although the embodiment of FIG. 9 shows the light detector and correct-for-drift feature both comprising fiber optic cables, other types of light detector components as are known in the art may be used.

Figure 10:
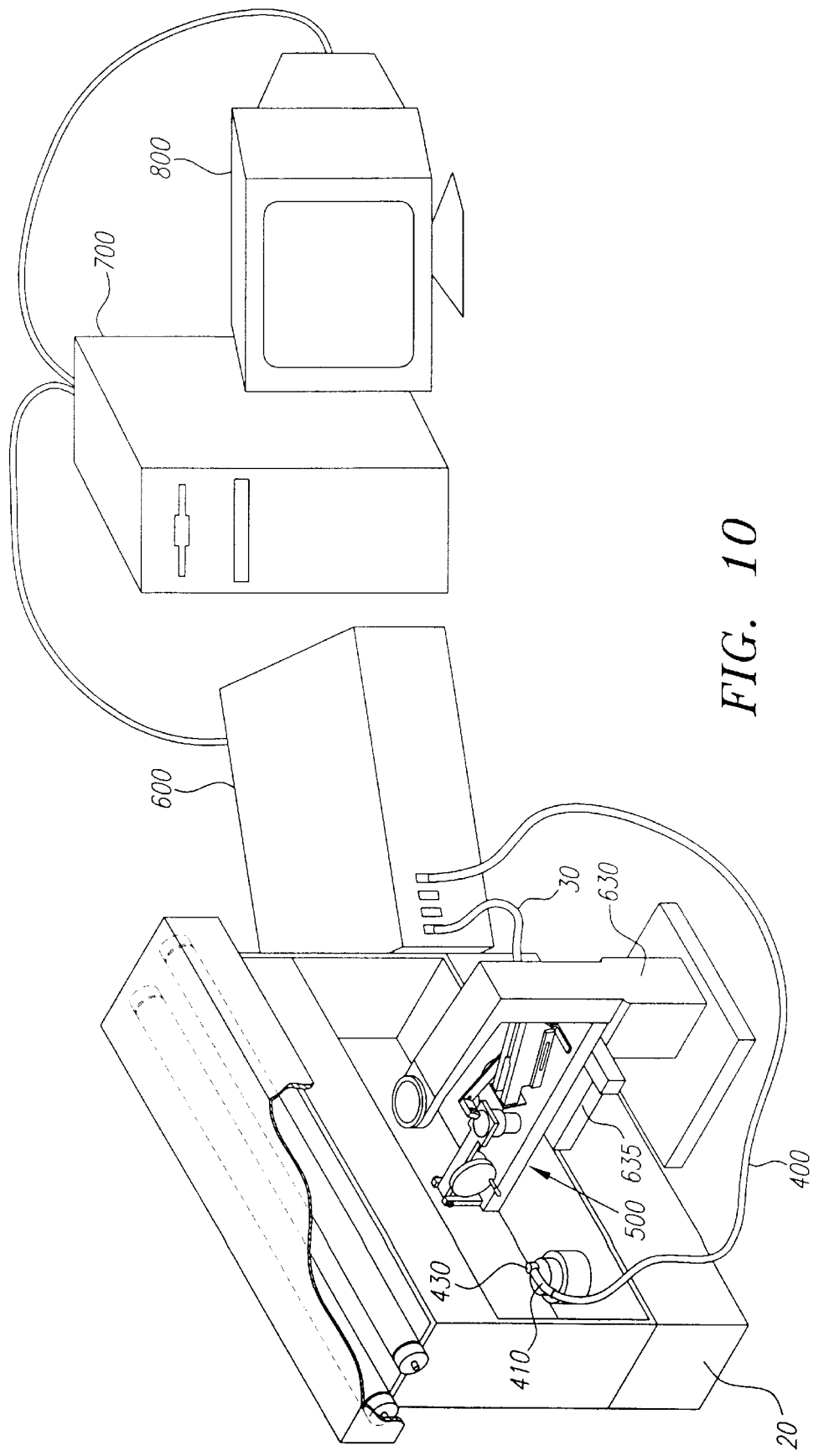
FIG. 10 shows an integrated view of the system of the present invention including the light box, measurement instrument, optical measurement device, data processor and monitor.

FIG. 10 shows an integrated view of one embodiment of the system of the present invention. The embodiment of FIG. 10 includes light box 20, measurement instrument 500, diode-array spectrophotometer 600, data processor 700 and monitor 800. FIG. 10 shows a particular embodiment of the system of the invention where the entire measurement instrument 500 of FIG. 5 is mounted on a microscope mount 630, having a mounting platform 635. The microscope mount may be used for height and distance adjustment of the measurement instrument with respect to the light source. The microscope mount may also control movement of the light detector comprising fiber optic 30 relative to the measuring chamber which is separately positioned in the light box. See e.g. FIG. 2. According to the embodiment of FIG. 10, the output of a light detector comprising fiber optic cable 30 is provided to an optical measurement device 600, preferably a spectrophotometer. Although, as shown in this embodiment, the light detector comprises a diode-array which is physically part of the optical measurement device, namely a diode-array spectrophotometer, the diode-array may alternately form part of the light detector housing along with the fiber optic cable. Alternately, the light detector may comprise a spectrophotometer with a collimator lens which detects light directly rather than through a fiber optic cable.

According to the embodiment shown in FIG. 10, the optical measurement device 600 provides measurement data to the optical analyzer, data processor 700, which in turn compares the measurement data against historical precedent and/or converts the measurement data into standard CIE color space. The data processor 700 may also assign the gemstone a color grade that accords with historical precedent or simply identify the gemstone. The results of the data processor's analysis may be optionally displayed on monitor 800, printed out on a printer or electronically stored. The measurement data itself may be graphically displayed in addition to, or in place of, the gemstone color assessment.

Figure 11:
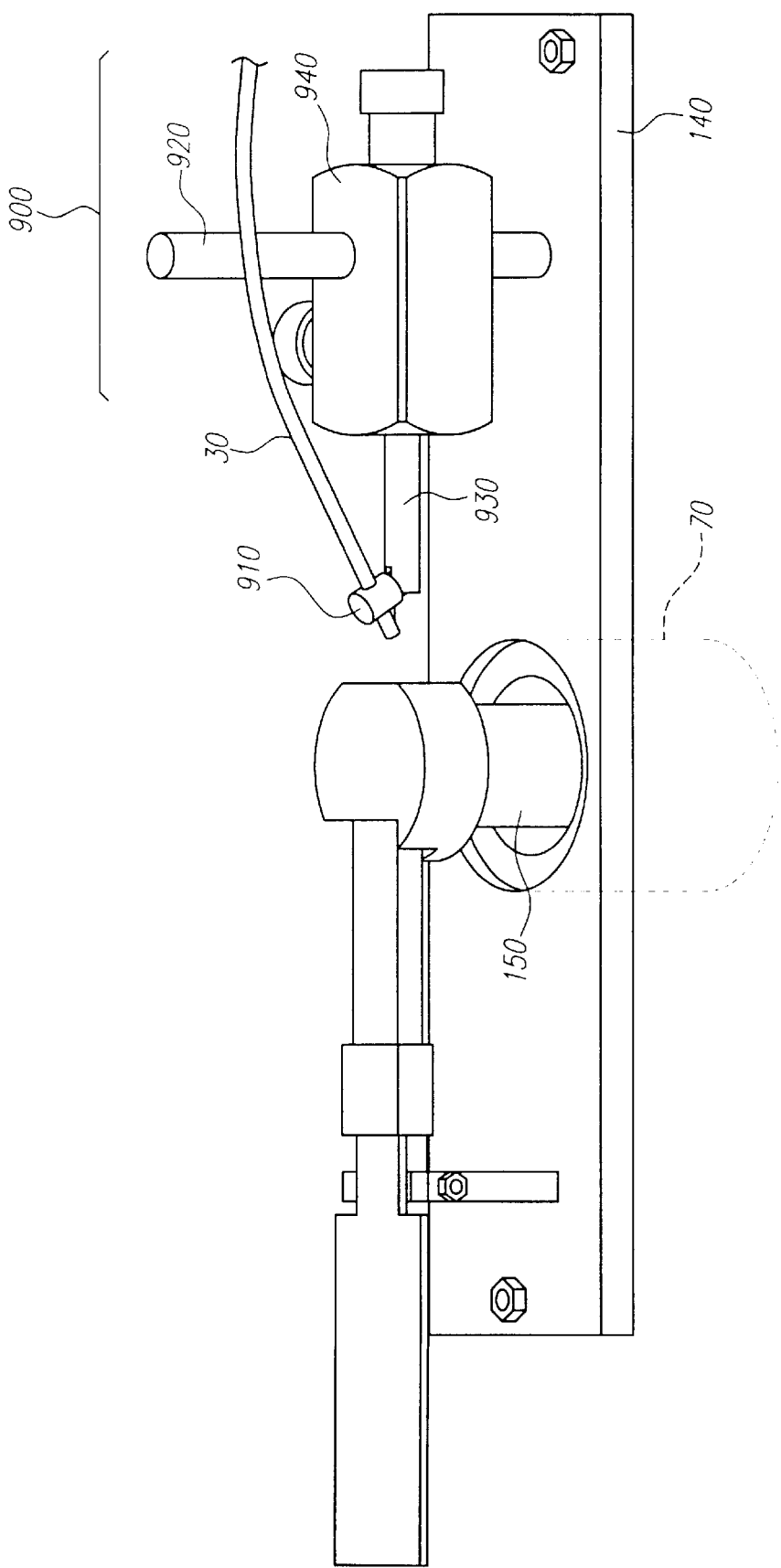
FIG. 11 shows an angle perspective view of an alternate embodiment of the invention wherein the measurement instrument is an integrated unit and the position of the light detector relative to the platform (not shown) is adjusted by a positioning assembly.

According to a preferred embodiment, shown in FIG. 11, height adjustment, angle adjustment, and distance adjustment for the light detector relative to the surface for accommodating the gem is achieved through a positioning assembly 900 which is mounted on base 140. FIG. 11 shows an integrated measurement instrument in which fiber optic cable 30 is secured to positioning assembly 900 by virtue of angle adjust 910. As shown in FIG. 11, angle adjust 910 is rotationally connected to the distance adjust 930 which in turn is moveable through the body 940 of positioning assembly 900 to facilitate adjustment of the distance of the light detector to the surface for accommodating the gem. Height adjust 920 likewise permits vertical movement of the body 940 to facilitate light detector height adjustment. In this manner the invention provides for a compact, fully adjustable, integrated measurement instrument which may be readily deployed in daylight-approximating illumination. Alternately, the light detector may be permanently fixed on the integrated measurement device at a proper angle, height and distance relative to the surface accommodating the gemstone. In a preferred embodiment, the light source itself forms a part of an integrated unit with the measurement instrument to make a self-contained illumination and measurement device. The integrated illumination and measurement device may also be of reduced size so as to be rendered portable.

Figure 12:
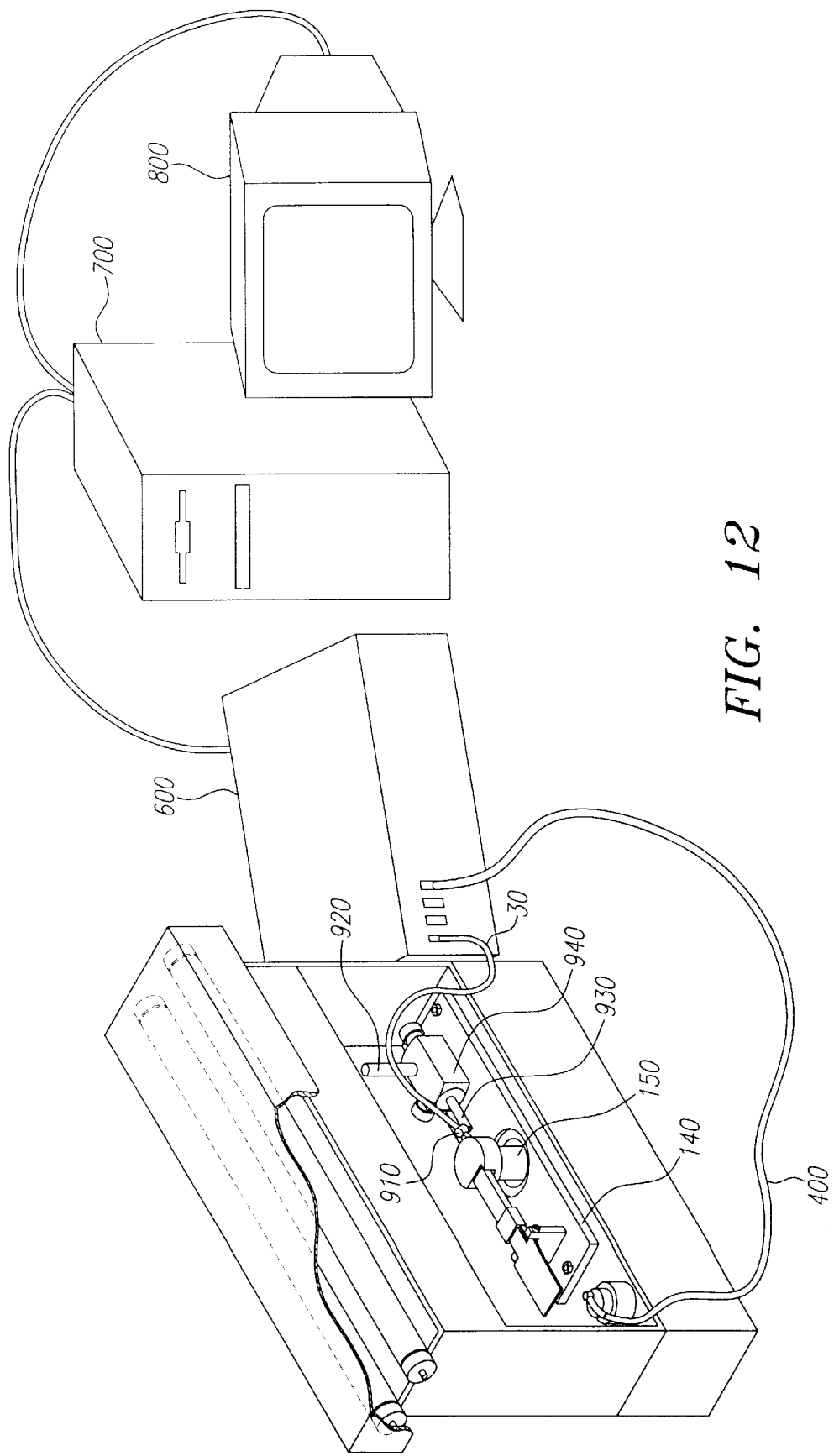
FIG. 12 shows the measurement instrument of FIG. 11 placed within the light box, ready for use.

FIG. 12 shows a preferred embodiment of the invention where the measurement instrument of FIG. 11 is placed in light box 20. As shown in the embodiment of FIG. 12, cylinder 150 extends from the floor of light box housing 20 and rotates rotor platform 50 (not shown) by virtue of rotor 70 deployed underneath the floor of light box housing 20. Base 140 of the measurement instrument has a circular opening which enables the measurement instrument to be securely placed over cylinder 150. Alternatively, in a non-rotating embodiment, the entire measurement instrument, including the platform, is freely placed within in light box 20. As above, the illumination source and measurement instrument may comprise an integrated unit.

Turning to exemplary methods of the invention, according to a preferred method, a diamond 40 is placed, table-down, on the rotor platform 50, illuminated with a daylight-approximating light source and rotated through three-hundred and sixty degrees, at a fixed speed, while light is detected by a light detector through an opening in the measurement chamber 110. The light detector transmits the illumination response of the gemstone to an optical measurement device 600 which in turn provides measurement data to a data processor 700. The data processor provides a final color assessment by averaging measurements taken during a three-hundred and sixty degree rotation of the gemstone. This rotational aspect of the invention improves repeatability of the result, particularly for poorly cut diamonds.

According to one aspect of the invention, the processor may average each measurement giving each one equal weight or, alternatively provide a weighted average. For example, the processor can provide a weighted average corresponding to the visual analysis positions used for visual analysis of fancy-shaped diamonds. For all gems, the processor may then convert the data to CIE color space and/or compare the data to historical precedent. Although measurements over the course of multiple rotations are contemplated by this method, to improve accuracy and reduce mechanical stress on the system, a minimal number of rotations of the gem stone are preferred and a single rotation is most preferred.

As far as materials are concerned, the diffuser of the present invention is preferably made of a thin PTFE sheet (approximately 0.4 millimeters thick) or other suitable equivalent material capable of reducing hindering effect of direct light reflections and dispersion. The material preferably has minimal absorption in the visible and near visible UV spectrum. Likewise, the measurement chamber and the rotor platform are preferably made of a diffuse, white reflectance material such as PTFE, although barium sulphate or Spectralon® may be used to the extent they have minimal specific absorption in the visible and near visible UV spectrum. The rotor of the invention preferably comprises a reliable mechanism for rotating the gem through three-hundred and sixty degrees, and most preferably comprises a continuous duty motor, such as a synchronic 3 Watt AC continuous duty motor.

In accordance with one object of the invention, in a preferred embodiment, the invention uses a high frequency ballast in combination with daylight-approximating fluorescent lamps in order to provide greater stability of light intensity and color distribution and improve the reliability of the measurement data. In a most preferred embodiment, the high frequency ballast has a frequency of approximately 30,000 and 70,000 Hz, and most preferably a frequency of approximately 35,000 Hz.

As disclosed herein, the invention has several advantages over prior systems, apparatuses and methods. First, because the light detection mechanism of the system approximates visual color analysis methodology used for gemstones, the invention comes closer to achieving visual color analysis results. Moreover, because the system of the present invention makes use of daylight-approximating light, the system achieves results more closely correlated with visual color analysis. Likewise, because the optical measurement device may make multiple measurements for a single rotation of the gem, for example using a fast spectrophotometric measurement device, the instrument results in extremely fast and reproducible color analysis. Finally, certain features of the invention, such as the diffuser, overcome substantial difficulties associated with approximating visual gem analysis methodology.

The inventions and concepts previously described may also be employed with modification to the analysis of fancy-colored diamonds and other colored gemstones. In a novel system employing these concepts to analyze fancy-colored diamonds and other colored gemstones, the detector of the invention preferably detects light coming from the crownside of the gemstone at a specific angle of between approximately 60 and 85 degrees relative to the gemstone's table. However, according to a preferred embodiment, the detector may detect light coming out of the fancy-colored diamond or colored gemstone at more than one angle, either sequentially or simultaneously, but within a specific angle range, preferably between approximately 60 and 85 degrees relative to the gemstone's table. The detection of a plurality of angles within a specific angle range may be accomplished by moving the detector during detection, using multiple detectors, using a wide angle detector and/or tilting the platform or other gem-accommodation surface during detection. If the detection of a plurality of angles within a specific angle range occurs sequentially, for a rotating gemstone the sequential change in angle preferably occurs after a complete rotation. According to this embodiment, in the case of the simultaneous detection, for a rotating gemstone the detector or detectors preferably detect a plurality of angles within the specific angle range within the course of a single rotation. The system further comprises a daylight-equivalent light source which illuminates the crown side of the gem in a diffused way.

While particular systems, instruments and methods have been described for measuring and analyzing the color of a gemstone, it will be apparent to those of ordinary skill in the art that other embodiments and alternative steps are possible without departing from the spirit and scope of the invention. For example, gemstones are often visually analyzed as to their fluorescence. The systems, instruments and methods may be novelly used to analyze the fluorescence color and fluorescence intensity of a diamond or other gemstone by using an ultraviolet light source rather than a daylight-approximating source and a detector capable of detecting fluorescence. It will be further apparent that certain features of each embodiment disclosed herein can also be used in combination with systems and instruments illustrated in other embodiments. Accordingly, the above description should be construed as illustrative, and not in a limiting sense, and the scope of the invention is defined by the following claims.

What is claimed is:

1. A diamond color measurement apparatus comprising:
   a daylight-approximating light source;
   a surface for accommodating a diamond;
   a light detector positioned to detect light from said light source coming out at a specific angle from the pavilion facets of a table-down diamond, when such a diamond is accommodated by said surface; and
   an optical measurement device for measuring light detected by said light detector.

2. A diamond color measurement apparatus comprising:
   a daylight-approximating light source;
   a surface for accommodating a diamond;
   a light detector positioned to detect light from said light source coming out at a specific angle from the pavilion facets of a table-down diamond, when such a diamond is accommodated by said surface,
   a diffuser; and
   an optical measurement device for measuring light detected by said light detector.

3. A diamond color measurement apparatus comprising:
   a daylight-approximating light source;
   a surface for accommodating a diamond;
   a light detector positioned to detect light from said light source coming directly from the pavilion facets of a table-down diamond, when such a diamond is accommodated by said surface; and
   an optical measurement device for measuring light detected by said light detector.

4. The diamond color measurement apparatus of claim 1, 2 or 3 wherein said light detect or is positioned so as to detect light directly coming from the pavilion facets of a tabledown diamond at an angle of between zero to approximately forty-five degrees relative to the table of a tabledown diamond, when such a diamond is accommodated by said surface.

5. A diamond color measurement apparatus comprising:
a daylight-approximating light source;
a surface for accommodating a diamond;
a light detector positioned to detect light from said light source coming out at a specific angle from the pavilion facets of a table-down diamond, when such a diamond is accommodated by said surface;
a diffuser positioned outside the path of detection of said light detector; and an optical measurement device for measuring light detected by said light detector.

6. The diamond color measurement apparatus of claim 1, 2 or 3 wherein said surface comprises a platform.

7. The diamond color measurement apparatus of claim 1, 2 or 3 wherein said surface comprises a rotor platform.

8. The diamond color measurement apparatus of claim 1, 2 or 3 wherein said surface comprises a rotor platform capable of rotating three-hundred and sixty degrees.

9. The diamond color measurement apparatus of claim 1, 2 or 3 further comprising a measurement chamber which at least partially envelops a diamond when such a diamond is accommodated by said surface.

10. The diamond color measurement apparatus of claim 1, 2 or 3 wherein said surface comprises a rotor platform and a rotor which may be set to permit measurement by said optical measurement device during one full rotation.

11. The diamond color measurement apparatus of claim 4 wherein said diffuser at least partially prevents light from directly illuminating a diamond when such a diamond is accommodated by said surface.

12. The diamond color measurement apparatus of claim 1, 2 or 3 wherein said surface is white reference for purposes of calibration.

13. The diamond color measurement apparatus of claim 1, 2 or 3 wherein said light detector is directed at a horizontal mid-point of a diamond when such a diamond is accommodated by said surface.

14. The diamond color measurement apparatus of claim 2 wherein said diffuser it a light transmitting diffuser.

15. The diamond color measurement apparatus of claim 5 wherein said diffuser is a light transmitting diffuser.

16. The diamond color measurement apparatus of claims 1, 2 or 3 wherein said light detector further comprises a collimator.

17. A system for diamond color measurement comprising:
a surface for accommodating a diamond;
a daylight-approximating illumination source for illuminating a diamond when the diamond is accommodated by said surface;
a light detector positioned to detect light coming out at a specific angle from the pavilion facets of a tabledown diamond when the diamond is accommodated by said surface; and
an optical measurement device for measuring light detected by said light detector.

18. A system for diamond color measurement comprising:
a surface for accommodating a diamond;
a daylight-approximating illumination source capable of illuminating a diamond accommodated by said surface;
a light detector positioned to detect light coming out at a specific angle from the pavilion facets of a table-down diamond accommodated by said surface;
a diffuser positioned between the illumination source and the diamond accommodated by said surface; and
an optical measurement device for measuring light detected by said light detector.

19. A system for diamond color measurement comprising:
a surface for accommodating a diamond;
a daylight approximating illumination source illuminating a diamond accommodated by said surface;
a light detector positioned to detect light coming directly from the pavilion facets of a table-down diamond accommodated by said surface; and
an optical measurement device for measuring light detected by said light detector.

20. The system for diamond color measurement of claims 17, 18 or 19 further comprising an optical analysis mechanism for processing measurements measured by said optical measurement device.

21. The system for diamond color measurement of claims 17, 18 or 19 wherein said surface comprises a rotor platform.

22. The system for diamond color measurement of claims 17, 18 or 19 wherein said light detector is positioned so as to detect light coming directly from the pavilion facets of a table-down diamond at an angle of between zero and approximately forty-five degrees relative to the table of a table-down diamond when such a diamond is accommodated by said surface.

23. A system for diamond color measurement comprising:
a surface for accommodating a diamond;
a daylight-approximating illumination source capable of illuminating a diamond accommodated by said platform;
a light detector positioned to detect light coming out at a specific angle from the pavilion facets of a tabledown diamond when the diamond is accommodated by said platform;
a diffuser positioned between said illumination source and said platform; and
an optical measurement device for measuring light detected by said light detector.

24. The system of diamond color analysis of claim 17, 18 or 19 wherein said light detector is rotatable about said surface.

25. A system for gem color measurement comprising:
a surface for accommodating a colored gem;
a daylight-approximating illumination source illuminating a colored gem accommodated by said surface;
a light detector positioned to detect light coming out at a specific angle from the crown facets of a colored gem when the gem is accommodated in the table-up position by said surface;
a diffuser positioned between said illumination source and said surface; and
an optical measurement device for measuring light detected by said light detector.

26. A system for gem fluorescence measurement comprising:
a rotating surface for accommodating a gem;
a light source for illuminating a gem accommodated by said rotating surface;
a detector positioned to detect light from said light source coming out at a specific angle from the crown facets of a colored gem accommodated in the table-up position by said surface;
a diffuser positioned between said light source and said surface;
an optical measurement device for measuring light detected by said light detector.

27. The diamond color measurement instrument of claim 3 further comprising a diffuser.

28. A method of analyzing the color of a non-fancy-colored diamond comprising the steps of:
- illuminating a table-down diamond with a diffuse daylight-approximating light source;
- detecting the light from the light source coming out at a specific angle from the pavilion facets of the diamond;
- measuring the detected light with an optical measurement device;
- analyzing the measurements with an optical analysis mechanism.

29. The method of analyzing the color of a non-fancy-colored diamond of claim 28 wherein said step of detecting comprises detecting light coming out of the pavilion facets of the diamond at an angle of between zero and approximately forty-five degrees relative to the table of the diamond.

30. The method of analyzing the color of a non-fancy-colored diamond of claim 28 further comprising the step of rotating said table-down diamond during said detecting step.

31. The method of analyzing the color of a non-fancy-colored diamond of claim 28 further comprising the step of rotating said table-down diamond a total of three-hundred and sixty degrees during said detecting step.

32. The method of analyzing the color of a non-fancy colored diamond of claim 28 wherein said step of illuminating comprises illuminating with a daylight-approximating light.

33. The method of analyzing the color of a non-fancy-colored diamond of claim 28 further comprising the step of placing the diamond, table-down, on a platform.

34. The method of analyzing the color of a non-fancy-colored diamond of claim 30 further comprising the step of placing the diamond on a platform enclosed.

35. The method of analyzing the color of non-fancy-colored diamond of claim 28 further comprising detecting light coming out at a second specific angle from the pavilion facets of the diamond.

36. The method of claim 35 wherein said step of detecting light coming out at a second specific angle occurs simultaneously with respect to said step of detecting light coming out at the first specific angle.

37. A method of analyzing the color of a non-fancy-colored diamond comprising the steps of:
- illuminating a tabledown diamond with a diffuse daylight-approximating light source;
- detecting light from the light source at a plurality of angles within a specific angle range from the pavilion facets a diamond;
- measuring the detected light with an optical measurement device; and
- analyzing the measurements with an optical analysis mechanism.

* * * * *